United States Patent [19]
Zeinalov et al.

[11] 4,227,020
[45] Oct. 7, 1980

[54] METHOD OF PREPARING NAPHTHENIC ACIDS

[76] Inventors: Bagadur K. Zeinalov, ulitsa Nizami 73, kv. 19; Vagab S. Aliev, ulitsa Nizami 66, kv. 10; Arif A. Akhundov, 5 Alatinskaya ulitsa, 3, kv. 13, all of Baku; Jury N. Bocharov, ulitsa Dokunina, 3, kv. 13, Moscow; Vladimir D. Lugovskoi, ulitsa Vurguna, 8/a, kv. 43; Akop A. Miramanian, 6 Mikroraion, 6, kv. 37, both of Baku, all of U.S.S.R.

[21] Appl. No.: 62,127

[22] Filed: Jul. 30, 1979

[51] Int. Cl.$^2$ .......................... C11C 1/00; C09F 5/08
[52] U.S. Cl. ................................ 562/511; 252/431 C
[58] Field of Search ................. 562/511, 408, 412; 252/431 C

[56] References Cited
U.S. PATENT DOCUMENTS

| | | | |
|---|---|---|---|
| 2,144,855 | 1/1939 | Rutherford | 562/511 |
| 2,519,309 | 8/1950 | Denton | 562/511 |
| 3,183,279 | 5/1965 | Mills | 562/412 |

*Primary Examiner*—John F. Niebling
*Attorney, Agent, or Firm*—Lackenbach, Lilling & Siegel

[57] ABSTRACT

A method for preparing naphthenic acids consists in that a petroleum fraction is oxidized at a temperature of 135°–140° C. in the presence of catalyst consisting of manganese naphthenate and potassium naphthenate; the obtained mixture of organic oxygen-containing compounds containing naphthenic and hydroxynaphthenic acids is diluted with an organic solvent, and the hydroxynaphthenic acids are precipitated and separated; the solution of the organic oxygen-containing compounds freed from hydroxynaphthenic acids in said organic solvent is treated with an aqueous solution of sodium hydroxide; thus obtained aqueous solution of sodium naphthenates is separated; said aqueous solution of sodium naphthenates is treated with diethyl sulphate at a temperature of 90°–95° C. to isolate ethyl naphthenates from which a fraction of ethyl naphthenate boiling out in a temperature range of 75°–170° C. is separated by rectification in vacuum of 3 mm Hg; the isolated fraction of ethyl naphthenates is treated with an aqueous solution of sodium hydroxide and the end product is isolated by the action of mineral acids.

1 Claim, No Drawings

METHOD OF PREPARING NAPHTHENIC ACIDS

FIELD OF THE INVENTION

This invention relates to petrochemical synthesis, and more particularly it relates to methods of preparing naphthenic acids. These acids are widely used in the manufacture of lacquers and varnishes, as the starting material for obtaining naphthenate siccatives which are actually salts of metals having variable valency and are used as additives to paints and varnishes. Naphthenic acids are also used for preparing alkyd resins which are the starting material for the manufacture of nitro enamels and paints. Lead naphthenates are effectively used for preparing printing paints. Naphthenates of cobalt, manganese, nickel, copper and of iron are used as catalysts in the synthesis and oxidation processes.

BACKGROUND OF THE INVENTION

Known in a prior art is the method for preparing naphthenic acids by oxidizing a petroleum fraction boiling out in a temperature range of 250°–500° C. with oxygen in the presence of a catalyst, a finely dispersed potassium permanganate (USSR Inventor's Certificate No. 137,515). According to this method, oxidized is the fraction comprising the following components, in percent by weight:

| | |
|---|---|
| naphthene hydrocarbons | 79 |
| paraffin hydrocarbons | 12 |
| aromatic hydrocarbons | 3 |

The acid value of said fraction is 32.2 mg KOH per gram of the fraction; its viscosity at a temperature of 50° C. is 59.4 centistokes. The petroleum fraction is oxidized at a temperature of 150° C. at an oxygen consumption of 0.25 cu.m per hour. The reaction continues for 32 hours; the catalyst consumption is 0.2 percent of the taken raw material.

The oxidation gives a complicated mixture of organic oxygen-containing compounds, among which there are acids of the aromatic, naphthenic and fatty series, the products of their peroxidation, viz., oxy acids, ether acids, keto acids, lactones and lactides.

The obtained mixture of oxygen-containing compounds is treated with a 20 percent aqueous solution of alkali. This treatment gives a mixture of alkaline salts of organic oxygen-containing compounds and unsaponifiable organic oxygen-containing compounds. Unsaponifiable oxygen-containing compounds are separated from the obtained mixture, for example, by extraction with organic solvents. The remaining mixture of the alkaline salts of organic oxygen-containing compounds is treated with a 30 percent sulphuric acid to separate a mixture of oxygen-containing organic compounds which include mono-, di- and poly-basic acids of the aromatic, naphthenic, and paraffin series; the mixture contains also non-oxidized materials.

The main disadvantage of this method is that the finely dispersed catalyst used in this process is not selective toward the process of preparing naphthenic acids. Moreover, another disadvantage of this method is that naphthenic acids are a component of a complicated mixture of oxygen-containing organic compounds, while high-quality naphthenic acids cannot be obtained by this process.

BRIEF DESCRIPTION OF THE INVENTION

The object of this invention is to provide a method for preparing naphthenic acids which would ensure high purity of the final product. Naphthenic acids result from the oxidation of a petroleum fraction boiling out in the temperature range of 250°–350° C., with oxygen in the presence of a catalyst at an elevated temperature. In accordance with the invention, oxygen required for the oxidation process is taken in the quantity of 0.06–0.065 kg/kg per hour and the process is carried out at a temperature of 135°–140° C. The catalyst used in the process is a mixture of naphthenates consisting of 30–40 percent by weight of manganese naphthenate and 60–70 percent by weight of potassium naphthenate, the catalyst being taken in the quantity of 1.5–2.5 percent of the weight of the starting petroleum fraction. The resultant mixture of organic oxygen-containing compounds containing hydroxynaphthenic and naphthenic acids is diluted with an organic solvent inactive toward said mixture, the solvent being taken in the weight ratio of 1:1–1.5. The dilution precipitates hydroxynaphthenic acids which are separated. The remaining mixture of organic oxygen-containing compounds in the solvent is treated with an aqueous solution of sodium hydroxide at a temperature at which the organic solvent boils. A solution of unsaponifiable organic oxygen-containing compounds in the organic solvent is separated from the obtained aqueous solution of sodium naphthenates. The aqueous solution of sodium naphthenates is treated with diethyl sulphate at a temperature of 90°–95° C. to obtain ethyl naphthenates from which the fraction of ethyl naphthenates boiling out at a temperature of 75°–170° C. is isolated by rectification in vacuum of 3 mm Hg. The isolated fraction is treated with an aqueous solution of sodium hydroxide and the end product is finally isolated from the obtained aqueous solution of sodium naphthenates by the action of mineral acids.

DETAILED DESCRIPTION OF THE INVENTION

The proposed method is realized as follows.

A petroleum fraction boiling out in a temperature range of 250°–350° C. is used as the starting material. The properties of the fraction are as follows: molecular mass, 220–240; specific gravity, 0.8520–0.8560; refractive index, 1.46–1.47; congealing point, minus 50° C.–55° C.; flash point, 110°–120° C. The Fraction comprises also the following main hydrocarbons, in percent by weight:

| | |
|---|---|
| aromatic | 0.1–2 |
| naphthenes | 70–75 |
| paraffins | 23–29.2 |

Each petroleum fraction is oxidized with oxygen at a temperature of 135°–140° C. The amount of oxygen used in the reaction is 0.06–0.065 kg/kg per hour. Oxidation is carried out in the presence of a catalyst, a mixture of naphthenates consisting of 30–40 percent by weight of manganese naphthenate and 60–70 percent by weight of potassium naphthenate. Said mixture is taken in the quantity of 1.5–2.5 percent of the weight of the starting petroleum fraction. The oxidation process is continued for 4–4.5 hours. The resultant product is a mixture of organic oxygen-containing compounds consisting of naphthenic, aromatic and fatty acids, products of their peroxidation, oxy acids, ether acids, keto acids, lactones and lactides. The acid value of said organic oxygen-containing mixture is 25–30 mg KOH per gram. Said mixture of organic oxygen-containing compounds comprises the following main compounds, in percent by weight:

| | |
|---|---|
| naphthenic acids | 15–16 |
| hydroxynaphthenic acids | 0.1–1 |
| unsaponifiable oxygen-containing organic compounds | 78–92 |

Said mixture of organic oxygen-containing compounds is diluted with an organic solvent, inactive toward the mixture, taken in the weight ratio of 1:1–1.5 with respect to the mixture. Said inert solvent may be, e.g. benzine, boiling out in the temperature range of 80°–170° C., or petroleum ether. On dilution with the organic solvent, hydroxynaphthenic acids are precipitated and separated by known methods, e.g. by filtration. The remaining solution of the mixture of oxygen-containing organic compounds freed from hydroxynaphthenic acid is treated with an aqueous, preferably 10 percent solution of sodium hydroxide, at a temperature of at which the solvent boils with stirring, for an hour. At the end of the alkali treatment the reaction mixture is settled to separate the solution of unsaponifiable organic oxygen-containing compounds in the organic solvent from the obtained aqueous solution of sodium naphthenates. The solvent is then separated from the unsaponifiable organic oxygen-containing compounds by distillation and returned to the stage of dilution of the mixture of organic-containing compounds. The aqueous solution of sodium naphthenates is treated with diethyl sulphate at a temperature of 90°–95° C. for 90–120 minutes continuously stirring the mixture. The mixture is then allowed to stand and the precipitated sodium sulphate is separated from ethyl naphthenates by known methods.

Ethyl naphthenates are distilled in a vacuum of 3 mm Hg, and the fraction boiling out in the temperature range of 75°–170° C. is collected. Said fraction is treated with an aqueous, preferably 10 percent solution of sodium hydroxide with simultaneous distillation of the formed ethyl alcohol. Mixtures of naphthenic acids are isolated by the action of mineral acids from the aqueous solution of sodium naphthenates. Sodium naphthenates are treated with a mineral acid to isolate free naphthenic acids. The obtained naphthenic acids have the following characteristics: purity (assay), 96.5–97 percent; unsaponifiable organic oxygen-containing compounds, 1.0–1.6 percent by weight; acid value, in mg KOH per gram of naphthenic acids, 230–260; color, by the iodimetric scale (amount of iodine in 100 ml of a 10 percent aqueous solution of potassium iodide), 20–22; specific gravity, 0.9521–0.9698; refractivity index, 1.4530–1.4649. The yield of naphthenic acids, calculated with reference to the starting petroleum fraction, is 2.73–3.98 percent by weight. The catalyst used in the process (the mixture of manganese naphthenate and potassium naphthenate) is a mixture of solid salts, readily soluble in petroleum hydrocarbons. The catalyst is prepared by the known method, described in the book by G. S. Petrov, A. I. Danilevich, and A. Y. Rabinovich "Development of Methods for Oxidation of Petroleum and Mineral Oils and Technical Uses of the Obtained Products," Goskhimizdat, Leningrad, 1933. The process of preparing the catalyst is illustrated by the following reactions:

$$RCOOH + KOH \rightarrow RCOOK + H_2O \qquad I$$

$$2RCOOK + MnSO_4 \rightarrow (RCOO)_2Mn + K_2SO_4 \qquad II$$

where RCOOH are naphthenic acids.

According to said reactions, naphthenic acid is neutralized with a 20 percent aqueous solution of alkali at a temperature of 80°–90° C. for an hour. A pre-calculated quantity of manganese sulphate is then added to the obtained mixture containing potassium naphthenate, and the exchange reaction is carried out at the same temperature for 90 minutes. The resultant product is manganese naphthenate.

The proposed invention has the following advantages.

Naphthenic acids obtained by the described method are highly pure (96.5–97 percent). The content of unsaponifiable organic oxygen-containing substances is low (1.0–1.6 percent by weight). The obtained naphthenic acids are clear homogeneous liquids suitable for use in the paint-and-lacquer industry. The catalyst used in the process is selective toward the process and ensures the production of naphthenic acids having from 12 to 15 carbon atoms.

For a better understanding of the invention, the following examples of its practical embodiment are given by way of illustration.

EXAMPLE 1

The properties of a petroleum fraction boiling in the temperature range from 250° to 350° C. are as follows:

| | |
|---|---|
| molecular mass | 224 |
| specific gravity | 0.8550 |
| refractive index | 1.468 |
| congealing point | −50° C. |
| flash point | 115° C. | group hydrocarbon composition, in percent by weight:

| | |
|---|---|
| aromatic hydrocarbons | 1.6 |
| naphthenes | 73.2 |
| paraffins | 25.2 |

The fraction taken in the quantity of 200 kg is oxidized with oxygen at a temperature of 135°–140° C., the oxygen consumption being 0.06 kg/kg per hour for the starting stock. The oxidation is effected in the presence of a catalyst, a mixture of manganese naphthenate and potassium naphthenate (35 percent and 65 percent respectively) taken in the quantity of 1.5 percent of the weight of the starting stock. The oxidation is continued for four hours. The resultant product of oxidation is 187.7 kg of a mixture of oxygen-containing organic compounds consisting of naphthenic, aromatic, and fatty acids, products of their peroxidation, oxy acids, ether acids, keto acids, lactones and lactides. The acid value of the oxygen-containing mixture is 28 mg KOH per gram. The obtained mixture of oxygen-containing organic compounds has the following composition, in percent by weight:

| | |
|---|---|
| naphthenic acids | 15 |
| hydroxynaphthenic acids | 0.9 |
| unsaponifiable organic oxygen-containing compounds | 79 |

The mixture of organic oxygen-containing compounds is diluted with 187.7 kg of a benzine fraction boiling in the temperature range from 80° to 170° C. Hydroxynaphthenic acids are precipitated and separated from the remaining solution of the mixture of oxygen-containing organic compounds. The hydroxynaphthenic acids can be separated by any known method, for example, by filtration. The quantity of the isolated hydroxynaphthenic acids is 1.7 kg.

The remaining benzine solution of the mixture of organic oxygen-containing compounds (375.4 kg) is treated with a 10 percent aqueous solution of sodium hydroxide taken in the quantity of 8.04 kg. The alkali treatment is carried out at a temperature of 80°–90° C. for an hour. The reaction mixture is allowed to stand. The benzine solution of unsaponifiable organic oxygen-containing compounds is separated from the aqueous solution of sodium naphthenates. The benzine solution is distilled to recover 185.5 kg of benzine which is resued at the stage of dilution of the mixture of organic oxygen-containing compounds. Another product of distillation is 148.3 kg of unsaponifiable organic oxygen-containing compounds, whose yield with respect to the total weight of the mixture of organic oxygen-containing compounds obtained at the stage of oxidation of the starting stock is 79 percent by weight.

The aqueous solution of sodium naphthenates is treated with 15.7 kg of diethyl sulphate and the reaction is carried out at a temperature of 90°–95° C. for 90 minutes. The reaction product is separated from sodium sulphate precipitate by settling. Said reaction product is ethyl naphtenates, the amount of which is 29.4 kg. The ethyl naphthenates are rectified in vacuum of 3 mm Hg to separate the fraction boiling out in the temperature range of 75°–170° C. The amount of the distilled product is 8.82 kg. Said fraction is treated with a 10 percent aqueous solution of sodium hydroxide taken in a quantity of 1.43 kg, and the formed ethyl alcohol is distilled simultaneously (2.9 kg). Next 1.74 kg of sulphuric acid are added to the remaining aqueous solution of sodium naphthenates to isolate 5.47 kg of naphthenic acids which are characterized by the following properties:

| | |
|---|---|
| purity (assay) | 96.5 percent |
| unsaponifiable organic oxygen-containing compounds | 1.3 |
| acid value, mg KOH per g | 245 |
| color (iodimetric scale) | 20 |
| specific gravity | 0.9679 |
| refractive index | 1.4638 |

The yield of naphthenic acids, calculated with reference to the starting petroleum fraction, is 2.73 percent.

EXAMPLE 2

The petroleum fraction boiling out in a temperature range from 250° to 350° C. has the following properties:

| | |
|---|---|
| molecular mass | 240 |
| specific gravity | 0.856 |
| refractive index | 1.47 |
| congealing point | −53° C. |
| flash point | 120° C. | group hydrocarbon composition, in percent by weight:

| | |
|---|---|
| aromatic hydrocarbons | 2.0 |
| naphthenes | 75 |
| paraffins | 23 |

The oxidation of the petroleum fraction, taken in the quantity of 200 kg is conducted at a temperature of 136° C., the oxygen consumption rate being 0.061 kg/kg per hour. The process is effected in the presence of a catalyst, a mixture of naphthenates consisting of 70 percent by weight of potassium naphthenate and 30 percent by weight of manganese naphthenate. The catalyst is taken in the quantity of 1.82 percent of the weight of the starting petroleum fraction. The oxidation is continued for 4.5 hours. The oxidation product is 190 kg of a mixture of organic oxygen-containing compounds whose acid value is 25 mg KOH per gram. The obtained mixture of oxygen-containing organic compounds has the following composition, in percent by weight:

| | |
|---|---|
| naphthenic acids | 16 |
| hydroxynaphthenic acids | 1 |
| unsaponifiable organic oxygen-containing compounds | 78 |

The obtained mixture is diluted with 190 kg of benzine to precipitate hydroxynaphthenic acids which are separated in a quantity of 1.9 kg. The benzine solution of oxygen-containing organic compounds (378.1 kg) is treated with a 10 percent aqueous solution of sodium hydroxide in a quantity of 8.12 kg. The sodium hydroxide treatment is carried out at a temperature of 80°–90° C. for an hour. The obtained reaction mixture is settled, and the benzine solution of unsaponifiable organic oxygen-containing compounds is separated from the aqueous solution of sodium naphthenates. The benzine solution is distilled to recover 185.7 kg of benzine, which is reused, and the separate 156 kg of unsaponifiable organic oxygen-containing compounds.

The aqueous solution of sodium naphthenates is treated with 15.82 kg of diethyl sulphate at a temperature of 90°–95° C. for two hours to obtain 29.7 kg of ethyl naphthenates, which are then rectified in a vacuum of 3 mm Hg to isolate the fraction boiling in the temperature range of 75°–170° C. The fraction (10.4 kg) is treated with a 10 percent aqueous solution of sodium hydroxide taken in a quantity of 1.7 kg. Ethyl alcohol (3.4 kg) is separated from the reaction products. Then 2.1 kg of phosphoric acid are added to the aqueous solution of sodium naphthenates to isolate 6.76 kg of naphthenic acids.

The obtained naphthenic acids have the following characteristics:

| | |
|---|---|
| purity (assay) | 97 per cent |
| unsaponifiable organic oxygen-containing compounds | 1.58 per cent by weight |
| acid value | 230 mg KOH per gram |
| color (iodimetric scale) | 22 |

| | |
|---|---|
| specific gravity | 0.9698 |
| refractive index | 1.4649 |

The yield of naphthenic acids, calculated with reference to the starting stock, is 3.38 percent by weight.

EXAMPLE 3

The petroleum fraction boiling in the temperature range of 250°–350° C. has the following characteristics:

| | |
|---|---|
| molecular mass | 220 |
| specific gravity | 0.852 |
| refractive index | 1.461 |
| congealing point | −55° C. |
| flash point | 110° C. | group composition, in percent by weight:

| | |
|---|---|
| aromatic hydrocarbons | 0.4 |
| naphthenes | 70.4 |
| paraffins | 29.2 |

The given petroleum fraction, taken in a quantity of 200 kg, is oxidized at a temperature of 138° C. at an oxygen consumption of 0.065 kg/kg per hour, in the presence of a catalyst consisting of 40 percent by weight of manganese naphthenate and 60 percent by weight of potassium naphthenate. The catalyst is taken in the quantity of 1.96 percent of the weight of the starting stock. The oxidation process is continued for 4.5 hours to give 189 kg of a mixture of organic oxygen-containing compounds whose acid value is 30 mg KOH per gram. The obtained mixture of organic oxygen-containing compounds has the following composition, in percent by weight:

| | |
|---|---|
| naphthenic acids | 15 |
| hydroxynaphthenic acids | 0.8 |
| unsaponifiable organic oxygen-containing compounds | 80 |

The obtained mixture is diluted with 189 kg of benzine to precipitate 1.5 kg of hydroxynaphthenic acids, which are then separated. The benzine solution of oxygen-containing organic compounds (376.5 kg) are treated with a 10 percent aqueous solution of sodium hydroxide taken in a quantity of 8.02 kg at a temperature of 80°–90° C. for an hour. The obtained reaction mixture is allowed to stand, and the benzine solution of the unsaponifiable organic oxygen-containing compounds is separated from the aqueous solution of sodium naphthenates. The benzine solution is distilled to recover 185.2 kg of benzine, which is then reused, and to obtain 151.2 kg of the unsaponifiable organic oxygen-containing compounds. The aqueous solution of sodium naphthenates is treated with 15.62 kg of diethyl sulphate at a temperature of 90°–95° C. for 90 minutes. The result of the reaction is 29.2 kg of ethyl naphthenates which are then rectified in a vacuum of 3 mm Hg to separate the fraction boiling in the temperature range of 75°–170° C. (9.34 kg) which is then treated with 1.46 kg of a 10 percent aqueous solution of sodium hydroxide. Ethyl alcohol is recovered from the reaction product in the quantity of 2.9 kg. The aqueous solution of sodium naphthenates is mixed with 1.64 kg of hydrochloric acid to isolate 5.5 kg of naphthenic acids.

The characteristics of thus obtained naphthenic acids are as follows:

| | |
|---|---|
| purity (assay) | 97 per cent |
| unsaponifiable organic oxygen-containing substances | 1.1 per cent by weight |
| acid value | 260 mg KOH per gram |
| color (iodimetric scale) | 22 |
| specific gravity | 0.9528 |
| refractive index | 1.4532 |

The yield of naphthenic acids, calculated with reference to the starting petroleum fraction, is 2.75 percent by weight.

EXAMPLE 4

A petroleum fraction boiling in the temperature range of 250°–350° C. has the following characteristics:

| | |
|---|---|
| molecular mass | 228 |
| specific gravity | 0.856 |
| refractive index | 1.4708 |
| congealing point | −55° C. |
| flash point | 115° C. | hydrocarbon composition, in percent by weight:

| | |
|---|---|
| aromatic hydrocarbons | 1.4 |
| naphthenes | 74.6 |
| paraffins | 24.0 |

The petroleum fraction, in a quantity of 200 kg is oxidized at a temperature of 135°–140° C., at an oxygen consumption of 0.06 kg/kg per hour in the presence of a catalyst consisting of 35 percent by weight of manganese naphthenate and 65 percent by weight of potassium naphthenate. The catalyst is taken in a quantity of 2.5 percent of the starting stock. The product of the oxidation reaction is 139.7 kg of a mixture of organic oxygen-containing compounds characterized by the acid number of 25 mg KOH per gram.

The obtained mixture of organic oxygen-containing compounds has the following composition, in percent by weight:

| | |
|---|---|
| naphthenic acids | 15 |
| hydroxynaphthenic acids | 0.1 |
| unsaponifiable organic oxygen-containing compounds | 82 |

The obtained mixture is diluted with 209.5 kg of petroleum ether to precipitate 0.2 kg of hydroxynaphthenic acids, which are separated by the known methods. The solution of organic oxygen-containing compounds in petroleum ether (349.2 kg) is treated with 3.98 kg of a 10 percent aqueous solution of sodium hydroxide at a temperature at which petroleum ether boils. The treatment is continued for an hour. The obtained reaction mixture is settled to separate the solution of unsaponifiable organic oxygen-containing compounds from the aqueous solution of sodium naphthenates. The separated solution of organic unsaponifiables in petroleum ether is distilled to recover 185 kg of the solvent, which is then reused, and to isolate 174.5 kg of the unsaponifiable organic oxygen-containing compounds. The aqueous solution of sodium naphthenates is treated with 15.6 kg of diethyl sulphate for 90 minutes at a temperature of 90°–95° C. to isolate 29.2 kg of ethyl naphthenates. Said ethyl naphthenates are rectified in a vacuum of 3 mm Hg of isolate the fraction boiling in the temperature range of 75°–170° C. (9.4 kg) which is treated with 1.5 kg of a 10 percent aqueous solution of sodium hydroxide. The result of the treatment with the alkali is the separation of 3 kg of ethyl alcohol. The aqueous solution of sodium naphthenates is mixed with 1.7 kg of sulphuric acid to isolate 7.97 kg of naphthenic acids.

The characteristics of thus prepared naphthenic acids is as follows:

| | |
|---|---|
| purity (assay) | 96.8 per cent |
| unsaponifiable organic oxygen containing compounds | 1.6 per cent by weight |
| acid value | 230 mg KOH per gram |
| color (iodimetric scale) | 22 |
| specific gravity | 0.9521 |
| refractive index | 1.4530 |

The yield of naphthenic acids, calculated with reference to the starting petroleum fraction, is 3.98 percent by weight.

What is claimed is:

1. A method for preparing naphthenic acids consisting in that a petroleum fraction boiling out in the temperature range of 250°–350° C. is oxidized with oxygen taken in the quantity of 0.06–0.065 kg/kg per hour at a temperature of 135°–140° C. in the presence of a catalyst consisting of 30–40 percent by weight of manganese naphthenate and 60–70 percent by weight of potassium naphthenate taken in the quantity of 1.2–2.5 percent of the weight of the starting stock; the product of the oxidation reaction, which is a mixture of organic oxygen-containing compounds containing naphthenic and hydroxynaphthenic acids, is diluted with an organic solvent taken in the weight ratio of 1:1–1.5 to the reaction mixture which is inert toward said mixture in order to precipitate hydroxynaphthenic acids which are then separated; the solution of organic oxygen-containing compounds in said organic solvent is treated with an aqueous solution of sodium hydroxide at a temperature at which said organic solvent boils to separate the obtained aqueous solution of sodium naphthenates from the solution of unsaponifiable organic oxygen-containing compounds in said organic solvent; said aqueous solution of sodium naphthenates is treated with diethyl sulphate at a temperature of 90°–95° C. to obtain ethyl naphthenates from which the fraction of ethyl naphthenates boiling out in the temperature range of 75°–170° C. is separated by rectification in vacuum of 3 mm Hg; said isolated fraction is treated with an aqueous solution of sodium hydroxide, and the end product is finally isolated from the obtained aqueous solution of sodium naphthenates by treating with organic acids.

* * * * *